(12) United States Patent
Kumar et al.

(10) Patent No.: US 7,445,932 B2
(45) Date of Patent: Nov. 4, 2008

(54) **DEVELOPMENT OF A HIGHLY EFFICIENT IN VITRO SYSTEM OF MICROPROPAGATION OF *SOLANUM VIARUM***

(75) Inventors: Anil Kush Kumar, Maharashtra (IN); Debasis Patnaik, Orissa (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 675 days.

(21) Appl. No.: 10/452,989

(22) Filed: Jun. 3, 2003

(65) Prior Publication Data

US 2003/0226180 A1    Dec. 4, 2003

Related U.S. Application Data

(60) Provisional application No. 60/385,141, filed on Jun. 3, 2002.

(51) Int. Cl.
*C12N 5/00*    (2006.01)
*C12N 5/02*    (2006.01)

(52) U.S. Cl. .................. 435/410; 435/420; 435/430; 435/430.1; 435/431

(58) Field of Classification Search .................. None
See application file for complete search history.

(56) References Cited

U.S. PATENT DOCUMENTS 5,514,580 A    5/1996    Oglevee-O'Donovan et al.

OTHER PUBLICATIONS

Tejavathi D.H. and Bauvana B. Micropropagation of *Solanum Viarum* Dunal through cotyledonary node, shoot tip and Nodal cultures. 1996 J. Phytol. Res. 9(2):101-105.*

Tejavathi D.H. and Bauvana B. In Vitro Morphogenetic studies in *Solanum Viarum* Dunal. 1998, J. Swamy Bot. Cl. 15 27-30.*
Makunga N.P. et al. Micropropagation of Thapsia garganica a medecinal plant 2003 Plant Cell Rep. 21:967-973.*
Hendrix Rose C. et al. In vitro organogenesis and plant regeneration from leaves of Solanum candidum Lindl., S.quitoeense Lam. and S. sessiliflorum Dunal. 1987. Plant Cell Tissue and Organ Culture 11 67-73.*
Arockiasamy D I. et al. Plant regeneration from node and Internode Explants of Solanum triblobatum I. 2002. Plant Tissue Cult. 12(2): 93-97.*
Smith Roberta H. Plant Tissue Culture. 2000. Techniques and experiments second edition. Academic Press. 37 43-58.*
Cappadocia et al. Plant regeneration from in vitro culture of anthers of Solanum chacoense Bitt. and interspecific diploid hybrids. Theor. Appl. Genet (1984) 69:139-143.*
P. V. Lakshmana Rao, Plant Science, vol. 98, Issue 2, 1994, pp. 193-198 (Submitted—Abstract only) Title : "In vitro regeneration of scented-leaved geranium Pelargonium graveolens".
Gauri Saxena, et al, Plant Science, 155 (2000) 133-140 Tilte:"An efficient in vitro procedure for micropropagation and generation of somaciones of rose scented Pelargonium".

* cited by examiner

*Primary Examiner*—Annette H Para
(74) *Attorney, Agent, or Firm*—J. Harold Nissen; Lackenbach, Siegel, LLP

(57) ABSTRACT

*Solanum viarum* is an alkaloid producing plant of the family Solanaceae with varied therapeutic uses. In order to grow the plant in large areas; one needs to have an efficient system of vegetative multiplication, which ensures its genetic uniformity, and true to the type nature. In nature largely seeds propagate plant, which could be result of cross-pollination which may result in genetic drift. The present invention provides an efficient micropropagation system, with high level of multiplication at relatively low cost of production. The multiplication ratio was as high as 1:6 and almost 95% the plants were viable and successfully cultivated in field. The present invention provides an ideal way of mass cultivation of the selected elite plant material.

9 Claims, 5 Drawing Sheets

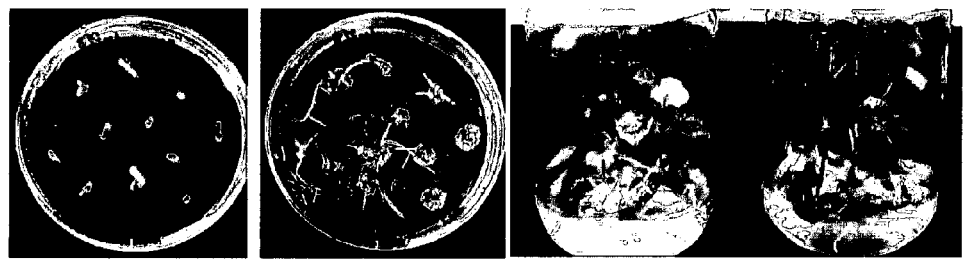
Fig 5 :     (a)            (b)            (c)            (d)

DEVELOPMENT OF A HIGHLY EFFICIENT IN VITRO SYSTEM OF MICROPROPAGATION OF *SOLANUM VIARUM*

CROSS REFERENCE TO RELATED APPLICATION

This invention claims priority from Provisional Patent Application Ser. No. 60/385,141 filed Jun. 3, 2002.

ADDITIONAL INFORMATION

This Application also includes information with respect to protection for a patent for a plant.

FIELD OF INVENTION

The present invention relates to the development of an efficient in vitro system of micropropagation of *Solanum viarum*.

BACKGROUND OF THE INVENTION

Plants have been one of the important sources of medicines ever since the dawn of human civilization. Human beings have been utilizing plants for basic preventive and curative health care since time immemorial. Recent estimates suggest that over 9000 plants have known medicinal applications in various cultures and countries. According to the WHO World Health Organization over 80 % of the world's population, or about 4.3 billion people, rely upon such traditional plant based systems of medicine to provide them with primary health care.

Demand for medicinal plants is increasing in both developing and developed countries due to growing recognition of natural products, being non-narcotic, having no side-effects, easily available at affordable prices, and sometimes are the only source of health care available to the poor. The medicinal plant sector has traditionally occupied an important position in the socio-cultural, spiritual and medicinal arena of rural and tribal lives of India. The medicinal plants sector in India supports primary health care needs of most of the country's population even today.

Chemically, depending on their active principles, plants may have alkaloids, glycosides, steroids or other groups of compounds, which may have marked pharmaceutical actions as anti-cancerous, anti-malarial, anti-helminthic or anti-dysenteric, etc. Among the most important materials with which pharmacologists manufacture drugs are alkaloids complex bio-compounds produced by many categories of plants. Plant alkaloids including cocaine, reserpine, quinine, ipecac, ephedrine, caffeine, nicotine etc. have many medicinal applications.

About 80% of all known green plants are flowering plants or angiosperms, most of which are found in the tropical rainforests of the world. Rainforest plants are rich in secondary metabolites, particularly alkaloids. Biochemists believe that alkaloid protect plants from disease value and benefit. Medicinal plants have thus gained pharmaceutical importance or therapeutic value due to the specific constituents or combination of secondary metabolites present in them. In some cases, changes in the relative proportion and quantity of secondary metabolites are often required for the improvement of therapeutic values of medicinal plants. Most of bio-molecules of the medicinal plants with therapeutic value are the secondary metabolites. These molecules are produced in very small quantities and in specific tissue of the plant. This makes their extraction process cumbersome and expensive.

Most researchers working in this area have so far and are still focussing on identifying tropical rainforest plants as a source of compounds useful for medicinal purposes, but have never attempted to identify common weed as its source. Till date tropical rain forest is considered important for medicinal plants, however common weeds have been neglected, which too have medicinal value. Medicinal Plants are far more likely to be weeds growing alongside a dirty road than in an exotic tropical jungle.

Weeds are the plants that thrive in the wild and can establish themselves quickly in relatively harsh agroclimatic conditions. The term "weed" in broadest sense implies to any plant growing where it is not wanted. Weeds can be native or non-native, invasive or non-invasive, and noxious or non-noxious. The weed used in the present invention is a non-invasive type. It is a known fact that weeds because of their genetic make up grow in the extreme climate. They relatively have higher concentration of secondary metabolites, which make them ideal source for genetic manipulation by modulation of the respective genes. While, considerable scientific attention has been given to the potential value of cultivated and tropical medicinal plants, very little research has been done on the potential of common weeds. *Solanum viarum* is one such neglected weed plants.

*Solanum viarum* belongs to the family of Solanaceae. *Solanum viarum Dunal* commonly known as "tropical soda apple" holds an important place as a source for production of medicinal drugs, due to relatively high level of steroidal alkaloids present in it. *Solanum viarum* can be cultivated on a wide range of soils under various agroclimatic conditions, but it cannot withstand waterlogging also the plant does not perform well in very clayey soils.

*Solanum viarum* yields a glycol-alkaloid, solasodine, a nitrogen analogue of diosgenine. Solasodine through 16-dehydro pregnenolone (16 DPA) is converted to a group of compounds like testosterone and methyl testosterone and corticosteroids like predinisolone and hydrocortisone. These steroidal compounds have anti-inflammatory anabolic and antifertility properties, due to which they are largely used in health and family planning programs all over the world. Solasodine presents several glucocorticoid like effects. It is effective against hypocholestrolamemic and antiatherosclerotic diseases. It enhances the glucocorticoid secretion by adrenal glands. In prolonged use, it causes atrophy of the adrenal gland cortex. Solasodine glycosides have an ability to check cytotoxicity of cancer cells.

In *Solanum viarum*, solasodine alkaloid is distributed throughout the fruits. It is however, established that about 60% of this is present the seeds and the remaining 40% in the pericarp. Generally, the accumulation of glycol alkaloid increases with the physiological age of the fruit and attains its peak value in the fruits of 50-60 days. This state of fruit growth coincides with the change in fruit colour from green to just yellow with streaks of green still present, after which the glycol alkaloid content falls gradually with the maturity of fruits. The crop takes about 6 months to be ready for harvesting. When, the crop is grown by adopting proper cultivation practices, it may yield nearly 10,000 kg/ha of fresh berries which, in turn, will give about 2500 kg/ha of dried berries. However considering the use of mature fruits as a source for production of medicinally important steroidal alkaloids, the availability of the seeds as a planting material is the most limiting factor for its cultivation.

Moreover, some *Solanum viarum* is a weed, and the seeds are the mode of multiplication which could result from a cross-pollination and may also result in genetic drift. This may affect the content of medicinally very important chemical constituents like solasodine. Therefore, there exists a need for an efficient system of vegetative multiplication which ensures its genetic uniformity and true to the type of nature.

Biotechnological tools are important to multiply, select, and conserve the critical genotypes of medicinal plants by adopting techniques such as micropropagation, creation of somaclonal variations and genetic transformation. Biotechnological tools can also be harnessed for production of secondary metabolites using plants as bioreactors. In-vitro propagation involves tissue culture system by multiplication of meristems and auxiliary buds. In many cases it provides opportunity to maintain true to type plant species and the propagation system can produce a large number of plants from a single clone.

Tissue culture is basically defined as in vitro growth of plantlets from any part of the plants in a suitable nutritive culture medium. It is also known as 'micropropagation' in scientific technology. Tissue culture is a means of preserving species that are rare and threatened and providing an alternative source of plants for commercial horticultural and traditional medicinal trade. Tissue culture involves the aseptic culture of plant protoplasts, cells, tissues, or organs on a culture medium. The cultures are maintained under controlled environmental condition. The main difficulty in conventionally growing indigenous plants in large quantities is to obtain sufficient plant material. Seeds may germinate erratically and bulbs usually propagate by offsets. This makes production too slow to warrant their introduction as new commercial crops. In vitro methods are therefore used to speed up propagation. The success of the system lies in the development of strict protocols for each species.

Micropropagation has been defined as in vitro regeneration of plants from organs, tissues, cells or protoplast and results in the true to type propagation of a selected genotype using in vitro culture techniques. In essence, tissue from a plant (explant) is isolated to create a sterile tissue culture of that species in vitro. Once a culture is stabilized and growing well in vitro, multiplication of the tissue or regeneration of entire plant can be carried out. Commonly shoots (tips, nodes or internodes) and leaf pieces are used however cultures can also be generated from many different tissues as well. Juvenile tissues generally respond best. With genotypes, the physiological age and origin of explants as well as the chemical composition of the culture medium and the physical environment of cultures have been found to influence growth and development of new plants in the culture system, hence one need to optimize these for each of the genotype.

In summary micropropagation of a given genotype, using tissue culture is targeted to achieve the following:

Rapid, large scale, year round production of desired plant species.

Propagation of plant species where, there is difficulty to grow the plants on large scale from seeds, because of the scarcity of seeds due to its use for other purposes.

Production of genetically uniform plant material (clones).

Production of disease free plant material.

Up to the present date, large-scale micropropagation using tissue culture of *Solanum viarum* has not been attempted, as *Solanum viarum* is a wild type of weed. Hence, not much attention has been paid to the improvement of the plant species in spite of important metabolites it produces. Also, there is no organized cultivation of this plant species for commercial utilization. It is simply collected from the wasteland or jungle. Therefore, there exists a need to develop an efficient in-vitro system for large-scale micropropagation of *Solanum viarum*.

OBJECTS OF THE INVENTION

Therefore, it is a principal object of the present invention to develop an efficient in-vitro micro-propagation system of *Solanum viarum* by plant tissue culture using various explants.

It is still an object of the present invention to identify explant, media and culture conditions for producing a large number of *Solanum viarum* plants by micropropagation.

It is a further object of the present invention to develop an economically viable method for in vitro micropropagation of *Solanum viarum*.

It is a further object of the present invention to provide a process for the regeneration of shoots of *Solanum viarum* plants in such a manner that they grow, develop healthy roots easily and efficiently to form fertile elite plant material.

It is a further object of the present invention to provide a process for the primary and secondary hardening of the tissue cultured plant material.

SUMMARY OF THE INVENTION

Accordingly the present invention is directed towards a novel method for efficient in-vitro large scale micropropagation of *Solanum viarum*.

The present invention provides identification of explant with the best regeneration and multiplication ability; optimization of composition of different culture media and combination of growth regulators; establishment of culture and hardening procedure for producing a large number of plants.

The present invention method of in-vitro micropropagation of *Solanum viarum* comprises of:

collecting the various explants from field grown plants or plants grown in a controlled green house environment or plant grown from seeds in an aseptic condition in test tubes;

cleaning and sterilizing the explants, inoculating the explants on an initiation medium comprising an MS medium supplemented with auxins like NAA 0.01-5 mg per liter, cytokiin like kinetin 1-10 mg per liter, or BAP 0.2-2 mg per liter, inositol 200-700 mg per liter along with various gelling agents selected from agarose, phytogel 0.3-1.0% and source of carbohydrate like sucrose 0.2-10 %;

incubating the explants inoculated on an initiation medium for a varied photoperiod of day ranging from 0-24 hours and night or dark period ranging from 24-0 hours for a period of 2-20 days at a temperature of 18-25 degrees centigrade; scoring the incubated plants for contamination if any, transferring healthy multiple shoots obtained form the explants with optimum growth to a multiplication and shoot elongation medium comprising an MS medium supplemented with inositol 200-700 mg per liter, auxins like IAA 0.01-0.2 mg per liter, or NAA 0.05-5.0 mg per liter; cytokinin like BAP 0.1-5.0 mg per liter, multiplying the cultures in the same medium and same culture conditions, and continuing the multiplication up to 12 cycles or until the vigor of the plant multiplication is diminished;

transferring the shoots of 3-6 cm height to a rooting medium comprising of MS medium of 0.1- 1.0 strength and maintaining till formation of well developed roots, removing the rooted plants planting on a soil mixture comprising of resterilized red soil, cocopeat and decomposed farm yard into 1:1:1 proportion and keeping in the green house with 70- 80% relative humidity, 40- 60% of the shade at a temperature of about 18- 28 degrees centigrade for primary hardening for 4-8 weeks, transferring the plants outside of the green house under a shade with 10- 50% light cut for a secondary hardening for 2-6 weeks, and transferring the plants to the field.

The multiplication ratio obtained with the present invention method was as high as 1:6 in per cycle. Thus the present invention provides a very rapid and efficient method of micropropagation for large scale multiplication of Solanum viarum.

The present invention's novel method for in-vitro micropropagation of *Solanum viarum* has the following advantages:

Rapid, large scale, year round production of the plant species.

Production of genetically uniform plant material.

Production of disease free plant material.

Simple to adopt at commercial scale and economical process.

BRIEF DESCRIPTION OF THE FIGURES

The following figures, which are in the form of photographs are part of the present specification and are incorporated to further, demonstrate certain aspects of the present invention. The invention may be better understood by reference to these figures in combination with the detailed description presented herein.

FIG. 1(*a*)—shows surface sterilized seeds.

FIG. 1(*b*)—shows germinated seed.

FIG. 1 (*c*)—shows shoot & root regeneration in the seedling.

FIG. 1 (*d*)—shows fully developed mother plant.

FIG. 5: depicts whole process of micropropagation from nodal segments.

FIG. 5 (*a*)—shows nodal segment with initiation at nodes.

FIG. 5 (*b*)—shows shoot regeneration and multiplication at nodal region.

FIG. 5 (*c*)—shows whole plant regeneration.

FIG. 5 (*d*)—Fully developed plant with roots ready for hardening.

Figure 1:
FIG. 1: depicts development of aseptic mother plant from seeds.
Figure 2:
FIG. 2: shows callus Induction from stem segments.
Figure 3:
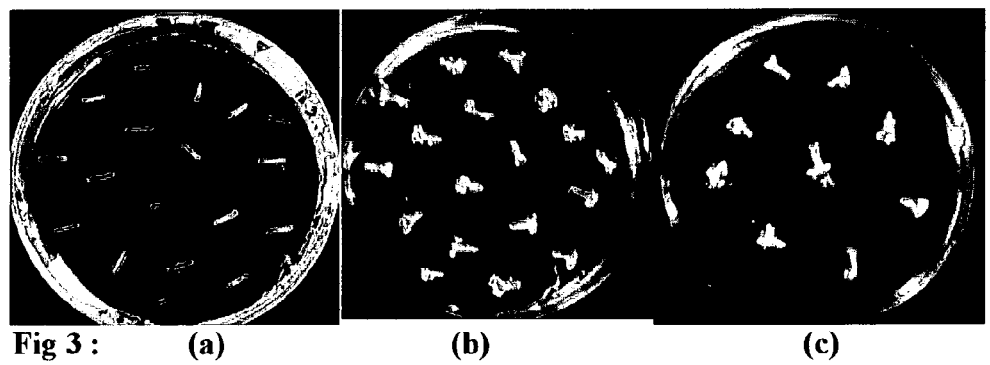
FIG. 3: shows petiole used as explants for regeneration.
Figure 4:
FIG. 4: shows leaf segments used as explants for regeneration.

The above figures are for the utility part of this Application and a set of black and white drawings are submitted.

DETAILED DESCRIPTION OF THE INVENTION

The present invention provides a novel highly efficient system of in-vitro micropropagation of *Solanum viarum*, for producing a large number of viable *Solanum viarum* by tissue culture techniques using various explants.

The inventors of the present invention have been successful in identifying an explant that when cultured in a suitable medium in the presence of a certain combination of growth regulators can stimulate a high level of differentiation of regenerates. The present invention thus provides an identification of a suitable explant as the starting material, optimization of composition of culture media and combination of growth regulators, establishment of culture and hardening procedure for producing a large number of plants. The present invention can be useful for:

an improvement of genotype by developing somoclonal variants through tissue culture;

development of a basic protocol for efficient regeneration which form the very basis of plant transformation;

modulating the production of secondary metabolites through transgenics; and micropropagation and selection of mutants through somaclonal variations.

Development of an efficient system of micropropagation of *Solanum viarum* is a critical feature of the present invention. In accordance with the process of the present invention which broadly, comprises of the following steps:

i. selecting the healthy plants of *Solanum viarum* growing in the field or in the green house in controlled environment or plants grown aseptically from seeds, in the culture tubes under controlled condition to serve as the mother plant;

ii. treating the plants growing in the field or green house with systemic fungicides and insecticides in a conventional manner and at one week interval, for two weeks;

iii. collecting the various explants from the *Solanum viarum* mother plants;

iv. cleaning the explants;

v. surface sterilizing the explants;

vi. cutting the explants into small pieces of approximately 2-10 mm length or diameter;

vii. inoculating the explants on an initiation medium comprising a modified MS medium supplemented with different concentration of growth hormones selected from auxins like NAA 0.01-5 mg per liter, cytokinins like BAP 0.2-2 mg per liter, or kinetin 1-10 mg per liter or the like and or combination thereof, inositol 200- 700 mg per liter along with various gelling agents selected from agarose, phytogel or the like and or combinations thereof in the range of 0.3-1.0%, and source of carbohydrate like glucose, sucrose, or the like and or combination thereof in the range of 0.2-10%;

viii. incubating the explants inoculated on the initiation medium for a varied photoperiod of day ranging from 0-24 hours and a night or dark period ranging from 24-0 hours for a period of 2-20 days at a temperature of 18- 25 degree centigrade; scoring the incubated plants for contamination if any;

ix. transferring the uncontaminated cultures to a growth room with light intensity of about 50-90 .mu.mol m.sup.-2s.sup-1 having about 10 -20 hours of light daily; at 18- 25 degrees centigrade temperature for at least 3- 9 weeks to give healthy cultures;

x. transferring the healthy cultures on the same medium and same culture conditions for the period of 2-6 weeks for further growth, evaluating the explant for their response after about 2-6 weeks, xi. harvesting the healthy multiple shoots with the optimum growth from particular explant, the said explant with the best growth being the nodal explants, xii. dissecting the multiple shoots into 0.4- 0.8 cm size and transferring to a multiplication and shoot elongation medium comprising an MS medium supplemented with inositol 200-700 mg per liter, growth hormones selected form auxins like IAA 0.01-0.2 mg per liter, NAA 0.05- 5.0 mg per liter, or the like and or combinations thereof, and cytokinins like BAP 0.1-5.0 mg per liter, xiii. incubating the cultures in the growth room with a light intensity of about 50-90 mu.mol m.sup.-2s.sup-1 having about 10- 20 hours of light daily; at 18- 25 degrees centigrade temperature for a period of 3- 6 weeks, multiplying the cultures in the same medium and same culture conditions, and continuing the multiplication up to 12 cycles or until the vigor of the plant multiplication is diminished, xiv. transferring the shoots of 3–6 cm height to a rooting medium comprising MS medium of 0.1 - 1.0 strength, and maintaining until the formation of well developed roots, xv. removing the rooted plants from the container, washing with water to remove agar adhering to the plant, drenching with a 0.02 - 0.2 % fumgicide like bavistin and planting on a soil mixture comprising pre sterilized red soil, cock peat and decomposed farm yard into 1:1:1 proportion and keeping the plants in the green house with 70 - 80 % relative humidity, 40 - 60 % of the shade at a temperature of about 18 - 28 degrees centigrade for primary hardening for 4-8 weeks, xvi. transferring the plants outside of the green house under the shade with 10-50% light cut or reduction for secondary hardening for 2–6 weeks, and xvii. transferring the plants to the field.

As a first step toward starting the micropropagation, the source of explant and its type becomes the thing of paramount importance. Using *Solanum viarum* mother plants according to the teachings of this invention, the, inventors have been successful in producing a large number of viable plants using micropropagation.

In accordance with teachings of the present invention the explants used are selected from leaves, leaf petioles, stem, stem internodes, stem nodal regions, seeds, apical buds, auxillary buds, or the like from *Solanum viarum* plants growing in the field or green house or plants grown aseptically from seeds in the culture tubes under a controlled environment. The preferable explants are stem nodal region, leaf and petiole segments, more preferably the explant is nodal region.

In an embodiment in accordance with the present invention explants were obtained from plants grown aseptically in the culture tubes, under controlled environment from seeds, to circumvent the problem of heavy systemic contamination. As, heavy loss of cultures due to the systemic microbial contamination was of a serious concern in certain instances when explants from the field grown plants were used. The said seeds used to grow plants serving as a source of explants were obtained from a self-pollinated plant grown in green house in controlled environment in order to maintain the genotype and develop the true to type resultant plants.

In accordance with the present invention for the treatment of the field grown *Solanum viarum* plants the systemic fungicides used is Bavistin, Captan, Dithane, Thiovit, or the like used at a concentration of 0.01-0.1% volume by volume basis and insecticides can be selected from Nuvacron, Fastac, Ultracid 40-WP, Thiodane or the like at a concentration of 0.01-0.1% volume by volume basis.

In accordance with the present invention cleaning of the explant comprises washing the explants thoroughly under running tap water, washing with 0.01- 0.2% Tween-20, followed by washing with distilled water, treating with disinfectant solution comprising systemic fungicides like bavistin 0.1%, contact fungicide like Indofil M-45 0.1% and systemic insecticide like Nuvacron 0.1%, for 10 minutes and repeatedly washing with sterilized distilled water to remove any traces of fungicide and insecticide. In case of seed explants immersing in 70% ethyl alcohol for 5 minutes and washing with autoclaved distilled water three times each lasting for 5 minutes.

In accordance with the present invention surface sterilization is carried out by treating the clean explant under laminar flow with mercuric chloride 0.01-1% for 2-10 minutes period, followed by multiple washing each for 2-20 minutes time period with sterile distilled water to remove the left over residues of mercuric chloride.

In accordance with the present invention another important aspect is the formulation of the culture media.

The present invention provides the specially designed initiation medium with optimized composition. In accordance with the present invention there is also been provided a single medium, which can induce both multiplication and the shoot elongation, for which the hormone concentration, which gave the maximum proliferation as well as the shoot elongation was selected. The use of the single medium for multiplication as well as shoot elongation helped in shortening the process and thereby saving the time and use of a medium for the "shooting" step, which is normally used in conventional micropropagation step. The use of the single medium also contributed towards making the process more economical. Furthermore the present invention also provides optimization of media for rooting.

In accordance with the present invention the initiation medium and multiplication and shoot elongation medium comprises of Murashige and Skoog (MS) basal medium with source of carbohydrate like glucose, sucrose, or the like; gelling agent selected from agar, phytogel or the like; supplemented with different concentration of inositol, growth hormones or additional components.

The basal MS medium that is Murashige and Skoog medium used in accordance with the present invention comprises of the following components,

| Components | Concentration (mg/l) |
| --- | --- |
| Sucrose | 30000 |
| Magnesium sulfate $(MgSO_4)7H_2O$ | 370 |
| Calcium chloride $(CaCl_2\ 2H_2O)$ | 400 |
| Potassium nitrate $(KNO_3)$ | 2000 |
| Ammonium nitrate $(NH_4NO_3)$ | 1500 |
| Potassium phosphate $(KH_2PO_4)$ | 50 |
| Ferrous sulfate $(FeSO_4\ 7H_2O)$ | 30 |
| Sodium ethylenediaminetetraacetic acid $(Na_2\ EDTA)$ | 30 |
| (Manganese sulfate)$MnSO_4\ 4H_2O$ | 20 |
| Zinc sulfate $(ZnSO_4\ 7H_2O)$ | 10 |
| Cupric sulfate $(CuSO_4\ 7H_2O)$ | 0.025 |
| Calcium Chloride $(CaCl_2\ 6\ H_2O)$ | 0.025 |
| Potassium Iodide (KI) | 0.5 |
| Boric acid $(H_3BO_3)$ | 5.0 |
| Molybdic acid sodium salt $(NaMoo_4\ 2H_2O)$ | 0.25 |
| Myo-Inositol | 100 |
| Glycine | 2.0 |
| Nicotinic acid | 0.5 |
| Phridoxine | 0.5 |
| Thiamine Hcl | 1.0 |

In accordance with the present invention the hormones commonly known as plant growth regulators employed in the initiation medium and multiplication and shoot elongation medium of the present invention may be selected from auxins or cytokinins or the like at various concentrations. Auxin may be selected from 2,4-Dichlorophenoxyacetic acid, indole acetic acid, indole-3-propionic acid, indole-3-butyric acid, indole-pyruvic acid, phenyl acetic acid, phenoxy acetic acid, naphthoxy acetic acid, naphthalene acetic acid, or the like. Cytokinin may be selected from zeatin, 2-ip, 6-benzyladenine, kinetin, or the like.

Another major aspect of the invention is hardening of tissue cultured micropropagated plants. Hardening of tissue cultured micropropagated plants could be a major constraint because of relatively high mortality and hence loss of the plantlets during this process. Depending on the plant material 10-90% losses during hardening have been documented. The inventors of the present invention have optimized the rooting medium/soil mixtures as well the growth environment in the green house to ensure proper root development which is crucial for the vigor and vitality of the plant and minimize the said losses during hardening. The hardening process involves primary hardening in the green house and the secondary hardening outside the green house. Primary hardening was targeted towards providing optimal conditions for root development like diffused/controlled light penetration, high humidity and conducive temperature. Secondary hardening being outside the green house involved gradual movement of the plants from the partial shade conditions to the natural open environment.

The multiplication ratio obtained with the present invention process was as high as 1:6. Thus the present invention provides very rapid and efficient and method for multiplication of *Solanum viarum*.

The advantage of the present invention micropropagation of *Solanum viarum* is that, it fills a long felt need for an efficient process for large scale multiplication and at the same time significantly lowers the production costs of commercial propagation of the said species.

As defined herein NAA is α-naphthalene acetic acid.
As defined herein IAA is Indole acetic acid
As defined herein BA is 6-Benzyladenine
As defined herein BAP is Benzyl amino purine
As defined herein MS medium is Murashige and Skoog's (MS) medium comprising of components of Murashige and Skoog's basal medium as defined in terms of their chemical composition and concentration.

The following examples are given by way of the illustration of the present invention. These examples should not be construed as limiting to the scope of the present invention.

EXAMPLES

Example 1

Identification of Explant:

According to the present invention to identify the explant with best regeneration and differentiation capacity, following experiment was conducted, Various explants namely leaf, stem, petiole and nodal segment were excised from the field grown plants or plants grown aseptically from the seeds in culture tubes in controlled environment. The explants were cleaned by washing with mild detergent like 0.01-0.2% Tween -20 followed by washing with distilled water. In order to remove the fungus or bacterial contaminants from the surface of the explants they were washed with systemic fungicide bavistin 0.01-0.2%, contact fungicide Indofil M-45 0.01-0.2%, systemic insecticide Nuvacron 0.01-0.2% and after each wash they were rinsed with distilled water to remove fungicide and insecticide. The explants were surface sterilized by treating the explant under laminar flow with mercuric chloride solution 0.01-1% for 2-10 minutes period, followed by multiple washing each for 2-20 minutes time period with sterile distilled water to remove the left over residue of mercuric chloride. The explants were then cut into small pieces of 2-10 mm length or diameter. The explants after dipping into double distilled water placed onto the initiation medium with the help of sterilized forceps in laminar flow. The initiation medium consisted of MS medium modified to have 500 mg per liter of inositol along with 5 mg per liter of kinetin and 1 mg per liter of Naphthalene acetic acid. Cultures were initially incubated in photoperiod of 24 hours of dark period at a temperature of 18-25 degrees centigrade for the period of 2-20 days. The culture tubes were transferred to growth room with light intensity of about 70 mu.mol m.sup.-2s.sup-1. and about 16 hours of light daily. Cultures were maintained for four weeks period to observe the relative regeneration and differentiation capacity of different explants cultured on the same medium and same condition. In case of stem and petiole as explant induction of callus was observed instead of direct regeneration. In case of leaf as an explant, some direct regeneration was noticed but frequency was too low in the range of 15-20%. Culturing of nodal segments gave the healthy multiple shooting at the nodal region, wherein the multiplication ratio was as high as 1:6.

Example 2

*Solanum viarum* seeds collected from self pollinated plants grown in controlled environment in green house were washed with distilled water, followed by 0.1% of Tween-20 for 5 minutes and final wash with distilled water. The seeds were treated with a disinfectant solution comprising bavistin 0.1%, Indofil M-45 0.1% and Nuvacron 0.1%, for 10 minutes and repeatedly washed with sterilized distilled water, followed by immersing in 70% ethyl alcohol for 5 minutes and washing with autoclaved distilled water three times each lasting for 5 minutes.

The seeds were then sterilized under laminar flow with 0.01% mercuric chloride for five minutes, followed by washing with sterilized distilled water for 5 times each lasting for 5 minutes to ensure that there is no residual left over of mercuric chloride on the seeds. Seeds under laminar flow, with the help of forceps, were placed onto Murashige & Skoog basal medium supplemented with sucrose 3% w/v and agar 0.8% w/v. for germination. Seeds were incubated at 25.±.2.degree. C. in white fluorescent light with intensity of 60 .mol m.sup.-2s.sup.-1 16 hr photoperiod. The cultures were continued till seeds germinated and seedlings were 1 week old.

2-3 week old seedlings were used as a source of explant. Stem nodal segments were excised from the seedling with the help of sharp scalpel and cut into pieces of about 5 mm length. Each piece was dipped into double distilled water and incubated onto initiation medium containing MS medium modified to have 500 mg per liter of inositol, 5 mg per liter of kinetin and 1 mg per liter of Naphthalene acetic acid. The cultures were incubated at 22.±.3 degree. C. in 24 hours of dark and 0 hour of day light period for one week period and scored for contamination if any. Uncontaminated cultures were transferred to growth room with 25.±.2 degree. C. temperature, 70 mu.mol m.sup.-2s.sup.-1. light and 16 hours of light daily. The cultures were maintained till multiple shoots were formed. These healthy multiple shoots if required were transferred to same medium and maintained under same condition for 3-6 weeks.

The healthy multiple shoots were taken out and cut into size of about 5 mm and transferred to multiplication and shoot elongation media containing MS medium supplemented with inositol 500 mg per liter, BAP 2 mg per liter and Indole acetic acid 0.025 mg per liter and incubated in the growth room with light of 70 mu.mol.m.sup.-2s.sup-1. intensity, 16 hours of photoperiod and 22.±.3 degree. C. temperature for period of 4 weeks. Cultures were multiplied on the same medium and in same culture conditions till 10 cycles or till the vigor of plant multiplication diminished.

The shoots of 3-4 cm size were taken out and transferred to Murashige & Skoog medium of 0.25 strength for rooting and maintained till formation of well-developed root system.

Rooted plants were taken out from the containers and washed with water to remove any agar attached to the plants. The plants were drenched with bavistin 0.1% and planted in a soil mixture containing pre sterilized red soil, cocopeat and decomposed farm yard in the ratio of 1:1:1 and kept in a green house with 70% relative humidity. 50% of the light shade and temperature of 22.±.3 degree. C. for primary hardening for 4 weeks.

Following primary hardening the plants were transferred outside the green house with 25% light cut for 4 weeks for secondary hardening.

Plants with 6-8 cm height or with 4-6 leaves after secondary hardening were transferred to field under drip irrigation.

Example 3

Micropropagation of *Solanum viarum* was carried out as per the method illustrated in example 2, as a whole, except for the initiation medium, wherein the composition contained MS medium modified to have 500 mg per liter of inositol, 3 mg per liter of kinetin and 1 mg per liter of Naphthalene acetic acid.

Example 4

Micropropagation of *Solanum viarum* was carried out as per the method illustrated in example 2, as a whole except for the initiation medium, wherein the composition contained MS medium modified to have 400 mg per liter of inositol, 5 mg per liter of kinetin and 1 mg per liter of Naphthalene acetic acid.

Example 5

Micropropagation of *Solanum viarum* was carried out as per the method illustrated in example 2, except for the composition of multiplication and shoot elongation medium which contained MS medium supplemented with inositol 500 mg per liter, 6-Benzylaminopurine 2 mg per liter and Indole acetic acid 0.05 mg per liter.

Example 6

Micropropagation of *Solanum viarum* was carried out as per the method illustrated in example 2, except for the composition of multiplication and shoot elongation medium which contained MS medium supplemented with inositol 500 mg per liter, 6-Benzylaminopurine 1.5 mg per liter and Indole acetic acid 0.05 mg per liter.

Example 7

Micropropagation of *Solanum viarum* was carried out as per the method illustrated in example 2, except for the composition of multiplication and shoot elongation medium, which, was similar to that in example 5 and rooting medium, which contained Murashige & Skoog medium of 0.5 strength.

Example 8

Micropropagation of *Solanum viarum* was carried out as per the method illustrated in example 2, except for the composition of multiplication and shoot elongation medium, which, was similar to that in example 5 and rooting medium, which contained Murashige & Skoog medium of 0.75 strength.

Example 9

Micropropagation of *Solanum viarum* was carried out as per the method illustrated in example 2, except for the composition of multiplication and shoot elongation medium, which, was similar to that given in example 4 and rooting medium, which, was similar to that in example 7.

Example 10

*Solanum viarum* stem nodal segments were excised from healthy plants grown in controlled environment in green house or those growing in the field. Prior to removal of stem nodal segments the plants were treated with bavistin and Nuvacron in conventional manner; at one week interval, for two weeks.

The excised stem nodal segments were washed with distilled water, followed by 0.1% of Tween-20 for 5 minutes and final wash with distilled water. They were then treated with a disinfectant solution comprising bavistin 0.1%, Indofil M-45 0.1% and Nuvacron 0.1%, for 10 minutes and repeatedly washed with sterilized distilled water, each wash lasting for 5 minutes.

The stem nodal segments were then sterilized under laminar flow with 0.01% mercuric chloride for five minutes, followed by washing with sterilized distilled water for 5 times each lasting for 5 minutes to ensure that there is no residual left over of mercuric chloride on the nodal segments.

Rest of the procedure was repeated as described under example 2 and with the composition of the media as employed in example 2-9.

Various modifications of the present invention in addition to those described and illustrated herein will be apparent to those skilled in the art from the foregoing description and examples. Such modifications are also intended to fall within the scope of the appended claims.

We claim:

1. A method for an efficient, in-vitro micropropagation of *Solanum viarum* producing a large number of viable plants, said method comprising the steps of:
   i. selecting a mother plant from healthy elite plants of *Solanum viarum* growing in a field to serve as a mother plant;
   ii. treating the plants growing in the field with systemic fungicides and insecticides in a conventional manner, at one week intervals, for two weeks;
   iii. collecting a nodal stem explants from the mother plants;
   iv. cleaning the collected explants;
   v. surface sterilizing the cleaned explants;
   vi. cutting the explants into small pieces of approximately 2-10 mm length or diameter;
   vii. inoculating the small pieces of cut explants on an initiation medium comprising an MS medium supplemented with the growth hormones like auxins selected from the group consisting of NAA, in the range of 0.01-5 mg per liter, cytokinins, selected from the group consisting of BAP 0.2-2mg per liter, and kinetin 1-10 mg per liter and/or a combination thereof;

viii. incubating the explants inoculated on the initiation medium for a varied photoperiod of a day or light period ranging from 0-24 hours and a night or dark period ranging from 24-0 hours and maintaining for a period of 2-20 days, and scoring the incubated inoculants for contamination if any;

ix harvesting healthy multiple shoots from the best responsive nodal explants;

x. dissecting the healthy multiple shoots into 0.4 -0.8 cm size and culturing on a multiplication and shoot elongation medium to a 3-6 cm. height, wherein the multiplication and shoot elongation medium is a single medium comprising an MS medium with a combination of IAA 0.025-0.1 mg/l and BAP 0.5-3 mg/ls supplemented with growth hormones like auxin selected from the group consisting of indole acetic acid, in the range of 0.01-0.2 mg per liter, cytokinin like BAP 0.1-5.0 mg per liter and/or combinations thereof, to give cultures;

xi. transferring the shoots of 3-6 cm height to a medium for rooting comprising an MS medium of 0.1-1.0 concentration strength and maintaining until the formation of a plant with well developed roots;

xii. removing the plants with well developed roots from a container, washing with water to remove agar adhering to the plant, drenching with 0.02-0.2% fungicide like bavistin and planting on a soil mixture for a primary hardening for 4-8 weeks;

xiii. transferring the plants outside of the green house for a secondary hardening for 2-6 weeks; and xiv. transferring the plants to a field.

2. The method, according to claim 1, wherein the systemic fungicides used for the treatment of the field grown *Solanum viarum* plants are Bavistin, Captan, Dithane, Thiovit, used at a concentration of 0.01-0.1% v/v.

3. The method, according to 1, wherein the insecticides used for the treatment of the field grown *Solanum viarum* plants are Nuvacron, Fastac, Ultracid 40-WP, Thiodane used at a concentration of 0.01-0.1% v/v.

4. The method, according to 1, wherein the cleaning of the explants comprises washing the explants thoroughly under running tap water, followed by washing with 0.01-0.2% Tween-20, rewashing with distilled water, treating with a disinfectant solution comprising systemic fungicides such as bavistin 0.1%, contact fungicide such as Indofil M-45 0.1% and systemic insecticide such as Nuvacron 0.1%, for 10 minutes and repeatedly washing with sterilized distilled water.

5. The method, according to 1, wherein the sterilization comprises treating the clean explant under a laminar flow with a 0.01-1% mercuric chloride solution for a 2-10 minute period, followed by multiple washing with sterile distilled water, each lasting for a period of 2-20 minutes.

6. The method, according to claim 1, wherein the NAA in the initiation medium is present in the range of 0.05-1.5 mg per liter.

7. The method, according to claim 1, wherein the kinetin in the initiation medium is present in the range of 2.5-7.5 mg per liter.

8. The method, according to 1, wherein the IAA in the multiplication and shoot elongation medium is present in the range of 0.025-0.1 mg per liter.

9. The method, according to 1, wherein the MS medium for the rooting has a concentration strength of 0.25-0.75 mg per liter.

* * * * *